US012623981B2

(12) United States Patent
    Ghosh et al.

(10) Patent No.: US 12,623,981 B2
(45) **Date of Patent: *May 12, 2026**

(54) INTEGRATION OF NAPHTHA TO ETHANE AND PROPANE FRACTIONATION SECTION WITH ETHANE STEAM CRACKER

(71) Applicant: UOP LLC, Des Plaines, IL (US)

(72) Inventors: Sudipta K. Ghosh, Haryana (IN); Xin X. Zhu, Des Plaines, IL (US); Kyle Cuellar, Fulshear, TX (US)

(73) Assignee: UOP LLC, Des Plaines, IL (US)

( * ) Notice: Subject to any disclaimer, the term of this patent is extended or adjusted under 35 U.S.C. 154(b) by 234 days.

This patent is subject to a terminal disclaimer.

(21) Appl. No.: 18/508,453

(22) Filed: Nov. 14, 2023

(65) Prior Publication Data

US 2024/0190792 A1     Jun. 13, 2024

Related U.S. Application Data

(60) Provisional application No. 63/431,558, filed on Dec. 9, 2022.

(51) Int. Cl.
    *C07C 4/04*      (2006.01)
    *B01D 3/14*      (2006.01)
    (Continued)

(52) U.S. Cl.
    CPC ..................................... *C07C 4/04* (2013.01)

(58) Field of Classification Search
    CPC .. C07C 4/04; C07C 7/04; C07C 5/327; B01D 3/007; B01D 3/141; B01D 3/143; C10G 7/00; C10G 9/36; C10G 69/06
    See application file for complete search history.

(56) References Cited

U.S. PATENT DOCUMENTS

2006/0135840 A1     6/2006   Reyneke et al.
2013/0213088 A1*    8/2013   Stylianou ............... F25J 3/0242
                                                        62/620

(Continued)

FOREIGN PATENT DOCUMENTS

WO        2006063201 A1     6/2006

OTHER PUBLICATIONS

International Search Report from corresponding PCT application No. PCT/US2023/082528, mailed Apr. 9, 2024.
(Continued)

*Primary Examiner* — In Suk C Bullock
*Assistant Examiner* — Jason Y Chong

(57)              ABSTRACT

A process of producing ethylene and propylene from naphtha, the process comprising: producing light paraffins—ethane, hydrogen/methane/residual ethane and propane rich streams—in a dividing wall fractionation column from a stream of hydrogen, methane, propane, and residual C4+ produced in the reactor section of a naphtha-to-ethane-and-propane processing unit by reacting naphtha with hydrogen, a naphtha reactor effluent stream produced by a naphtha reactor of the naphtha-to-ethane-and-propane processing unit is cooled to produce a feed stream. The feed stream is passed to a dividing wall fractionation column. An ethane stream from the dividing wall fractionation column is passed to an ethane steam cracker to produce a cracking heater effluent stream. The cracking heater effluent stream is passed to a coldbox of the ethane steam cracker after multiple steps such as quenching, compression, cooling, caustic scrubbing, drying. One or more fluids for cooling the naphtha (NEP) reactor effluent stream and for cooling the coldbox of the ethane steam cracker are provided by a common refrigeration system.

19 Claims, 5 Drawing Sheets

(51) Int. Cl.
  *C07C 5/327*          (2006.01)
  *C10G 9/36*           (2006.01)

(56)                References Cited

U.S. PATENT DOCUMENTS

2015/0299067 A1    10/2015  Kloth et al.
2016/0369186 A1    12/2016  Dittrich et al.
2016/0369191 A1    12/2016  Ward et al.
2020/0399546 A1*   12/2020  Van Willigenburg ......................
                                          C10G 69/06

OTHER PUBLICATIONS

Written Opinion from corresponding PCT application No. PCT/
US2023/082528, mailed Apr. 9, 2024.

* cited by examiner

INTEGRATION OF NAPHTHA TO ETHANE AND PROPANE FRACTIONATION SECTION WITH ETHANE STEAM CRACKER

RELATED APPLICATIONS

This application claims the benefit of and priority to U.S. Provisional Patent Application No. 63/431,558 filed on Dec. 9, 2022, the entirety of which is incorporated herein by reference.

TECHNICAL FIELD

This invention relates generally to separating ethane and propane from an effluent stream of a naphtha to ethane and propane reactor section; more particularly, the invention relates to separating streams rich in ethane, hydrogen/methane and propane from the effluent using a dividing wall fractionation column (DWC), optimized routing of ethane and hydrogen/methane streams to an ethane steam cracker to a most suitable location within the steam cracker.

BACKGROUND

Naphtha fed to a naphtha cracker produces olefins, namely ethylene and propylene. There is an industry trend towards shifting refining capacity to make increased petrochemicals due to the high value and market demand of ethylene and propylene compared to fuels. Naphtha steam cracking is the industry standard for making ethylene and propylene from naphtha, but ethylene plus propylene yields are low—less than 60% and typically less than 50% by weight depending on naphtha composition.

The naphtha-to-ethane-and-propane (NEP) unit is designed to preferentially produce ethane and propane from naphtha via reacting naphtha with hydrogen. Ethane fed to an ethane steam cracker (ESC) and propane fed to a propane dehydrogenation unit (PDH) produces higher quantities of olefins (ethylene and propylene) than what would be possible if naphtha is directly fed to a naphtha cracker to produce olefins.

However the products of NEP contain light ends (hydrogen, methane) along with ethane and require refrigeration utilities for separation. Separation of these components is essential but energy intensive and require refrigeration—so that ethane, the preferred feed component can be fed to the ESC.

The present invention is provided to solve the problems discussed above and other problems, and to provide advantages and aspects not provided by prior process and apparatuses of this type. A full discussion of the features and advantages of the present invention is deferred to the following detailed description, which proceeds with reference to the accompanying drawings.

SUMMARY

A process of producing ethylene and propylene from naphtha, the process comprising: a process of producing light paraffins from naphtha by processing the effluent stream of NEP reactor and comprising of hydrogen, methane, ethane, propane and residual C4+s. This stream is fed to a dividing wall fractionation column (DWC). An ethane stream is separated in the dividing wall fractionation column as a side-cut product. The other streams separated in the DWC is a top product of hydrogen, methane and residual ethane and a bottom product of propane and residual C4+

The ethane stream is passed to an ethane steam cracker to produce cracking heater effluent comprising ethylene, unreacted ethane, hydrogen, methane, and other components. The cracking heater effluent is passed through a series of steps of the ethane steam cracker, compressed in a compression train, caustic scrubbed, dried and cooled in a coldbox. In the coldbox, a hydrogen rich stream is separated and a methane rich stream is separated via demethanizer overhead. The demethanizer bottom stream is deethanized, processed in an acetylene convertor reactor (to convert the acetylenes) and routed to a C2 splitter. This stream comprises of ethylene and unreacted ethane stream. The ethane and ethylene are separated in the C2-splitter column to produce ethylene product and ethane is recycled back to the cracking heaters. The DWC top product comprising of hydrogen, methane and residual ethane is fed directly to the aforementioned compression train of the ESC where the components are separated along with similar components from the ESC cracking heater effluent. One or more fluids for cooling the feed stream comprising hydrogen, methane, ethane, and propane to the dividing wall fractionation column in a coldbox exchanger, for cooling a condenser of the dividing wall column fractionation column, and are provided by a common source of refrigeration fluid—used by the cold box and other cooling exchangers of the ethane steam cracker as well.

Other features and advantages of the invention will be apparent from the following specification taken in conjunction with the following drawings.

BRIEF DESCRIPTION OF THE DRAWINGS

One or more exemplary embodiments of the present invention will be described below in conjunction with the following drawing figures, in which.

DETAILED DESCRIPTION

Figure 1:
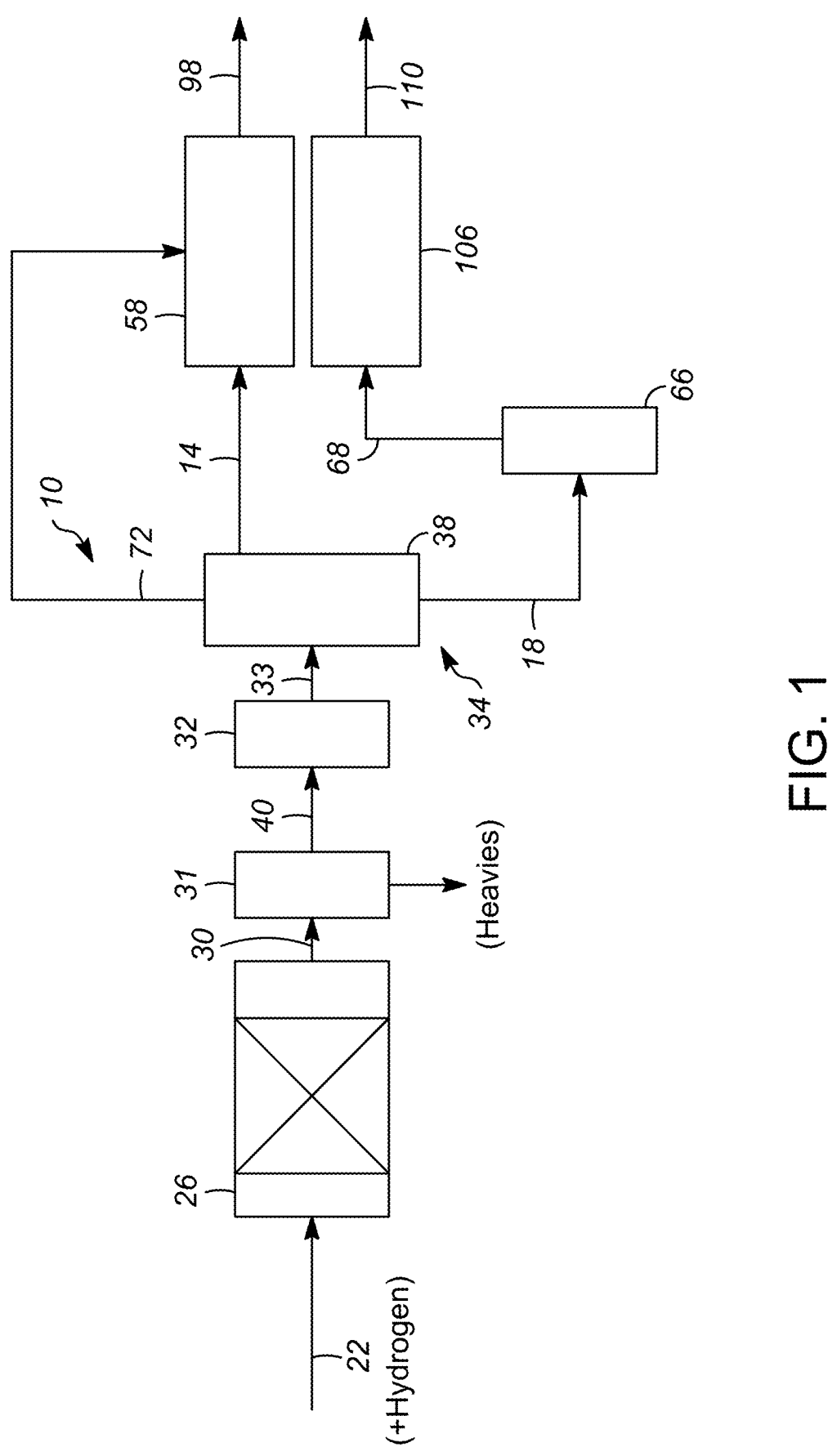
FIG. 1 is a schematic of a naphtha-to-ethane-and-propane processing unit with a separation section.

The term "downstream" means that at least a portion of fluid flowing to the subject in downstream may operatively flow from the object with which it fluidly communicates.

The term "upstream" means that at least a portion of the fluid flowing from the subject in upstream may operatively flow to the object with which it fluidly communicates.

The term "direct" means that fluid flow from the upstream component enters the downstream component without passing through any other intervening vessel.

The term "indirect" means that fluid flow from the upstream component enters the downstream component after passing through an intervening vessel.

The term "bypass" means that the object is out of downstream communication with a bypassing subject at least to the extent of bypassing.

As used herein, the term "rich" is defined as at least 50 mol %.

As mentioned above, a process and method for separating effluent from a naphtha-to-ethane-and-propane (NEP) reactor section—for which the feed is naphtha, into ethane, propane, and hydrogen/methane rich streams is described. With these general principles in mind, one or more embodiments of the present invention will be described with the understanding that the following description is not intended to be limiting.

This disclosure is directed to a process of producing light paraffins from naphtha from a stream comprising hydrogen, methane, and ethane, propane and C4+ produced in a reactor section of a naphtha-to-ethane-and-propane processing unit, including a process of separating hydrogen, methane, ethane, propane and C4+ hydrocarbons in a deethanizer column configured as a dividing wall column (DWC), which is part of a fractionation section of a naphtha-to-ethane-and-propane (NEP) processing unit. The ethane and propane form feedstocks for an ethane steam cracker (ESC) and a propane de-hydrogenation unit (PDH). The propane dehydrogenation is a process in which light paraffins such as propane can be dehydrogenated to make propylene. Dehydrogenation is an endothermic reaction which requires external heat to drive the reaction to completion. This configuration is part of an overall scheme to feed ethane to the ESC and propane to the PDH, as this enhances an increased efficiency of production of ethylene and propylene (light olefins) from the naphtha than would be possible if naphtha is fed directly to a steam cracker to produce the light olefins.

The NEP processing unit is designed to preferentially produce ethane and propane from naphtha via reacting naphtha with hydrogen. An ethane rich stream is fed to an ethylene producing unit, for example an ESC and a propane rich stream is fed a PDH. This configuration produces higher quantities of olefins, namely ethylene and propylene, than what would be possible if naphtha was directly fed to a naphtha cracker to produce olefins.

An NEP system comprises a reactor section and a fractionation section. In the reactor section, naphtha is reacted with hydrogen. An NEP reactor effluent comprises of hydrogen, methane, and substantial volumes of ethane and propane, as well as C4 paraffins and other C5 to C9+ hydrocarbon components, including C5 paraffins and C6/C7/C8/C9+ aromatics.

Figure 3:
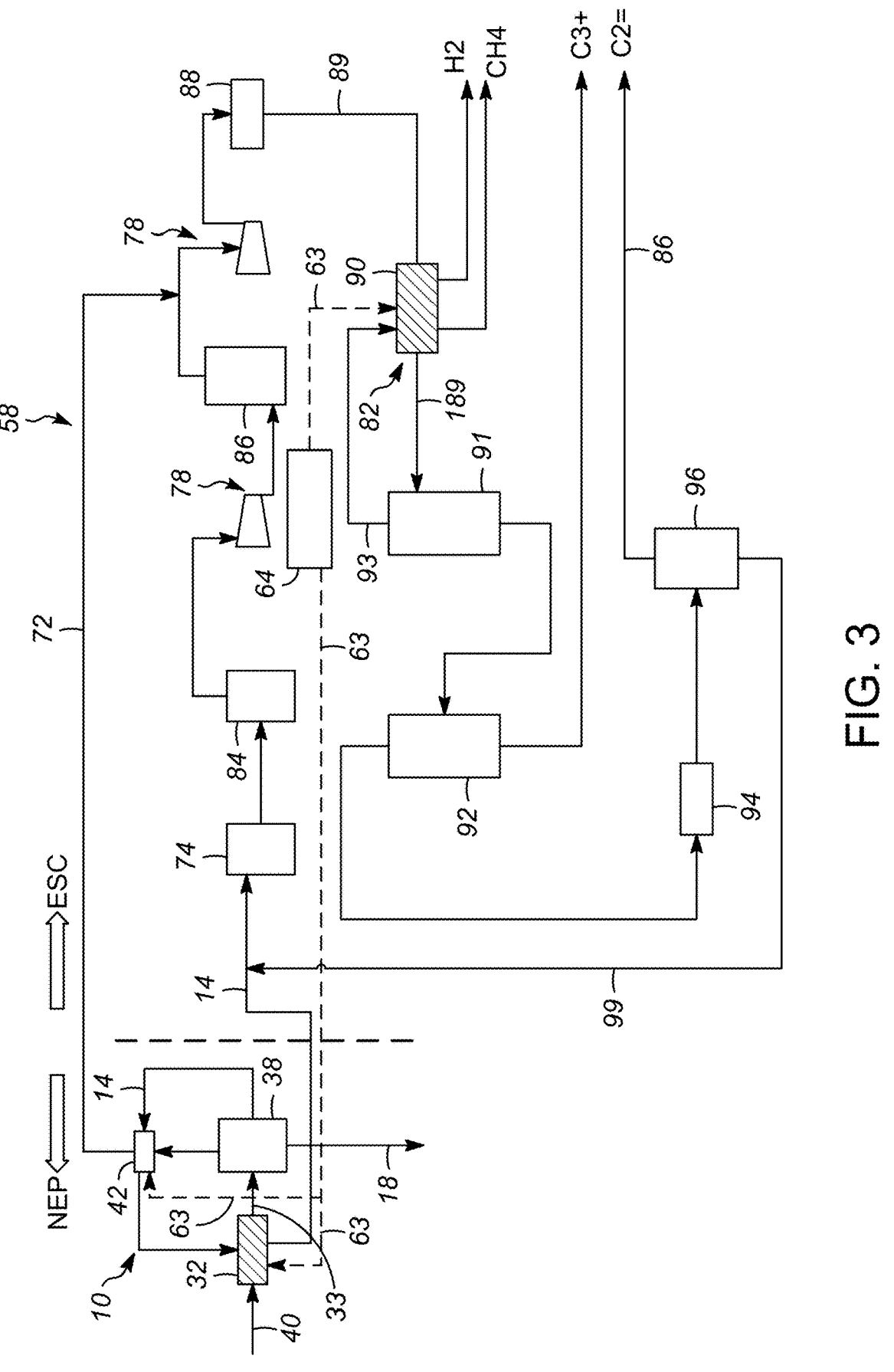
FIG. 3 is a schematic of a naphtha-to-ethane-and-propane processing unit in combination with an ethane steam cracker featuring separate coldbox heat exchangers in the naphtha-to-ethane-and-propane processing unit and the ethane steam cracker having a common source of refrigeration fluid for the coldbox heat exchangers.

The NEP fractionation section separates the reactor effluent stream into the following streams for further processing in downstream units:

a) An ethane rich stream, which is passed to the ESC to produce ethylene in cracking heaters of the ESC. The effluent stream from the ESC cracking heaters also contain hydrogen, methane, unreacted ethane, and some C3+ components. The effluent stream is cooled and quenched, caustic scrubbed, and compressed in a cracked gas compressor train. This compressed stream is subsequently fractionated in the fractionation section of the ESC using fractionating columns and refrigeration to cool the streams so that the very light boiling components can be separated. Apart from the main product, ethylene, the other product streams from the ESC include hydrogen, methane, ethane and C3+ stream. The ethane is recycled to the cracking heaters for further production of ethylene. FIG. 3 shows a schematic of an ESC. An ethane rich stream from the NEP processing unit 10 is first fed a cracking heater section of the ESC (see FIG. 3).

b) A stream comprising of hydrogen, methane, and some ethane, which is also processed in the ESC. This stream joins the ESC in the cracked gas compressor train, upstream of the cold fractionation section of the ESC. The hydrogen and methane leave the cold fractionation section while the ethane is recovered in a C2-splitter of the ESC and is recycled to the ethane cracking heaters.

c) A propane rich stream with some C4+ components is fed to a propane dehydrogenation unit (PDH) after separating the propane in a depropanizer.

The above streams a) through c) are separated in a deethanizer column of the NEP. The deethanizer column 38 is configured as a DWC. In addition to streams a) through c), the NEP fractionation section produces two other streams:

d) A C4 rich stream;

e) An aromatics byproduct stream.

The separation of these streams are relatively simple and are not part of this invention disclosure Referring to FIG. 1, generally, an NEP processing unit 10 is designed to preferentially produce an ethane rich stream 14 and a propane rich stream 18 from a naphtha stream 22 via reacting naphtha with hydrogen in a NEP reactor 26. An NEP reactor effluent stream 30 comprising a mix of hydrogen, light paraffin stream (predominantly ethane and propane) and also some C4+ components is discharged from the NEP reactor 26.

The naphtha stream 22 may comprise C4 to C12 hydrocarbons preferably having a T10 between about 0-10° C. and about 60° C. and a T90 between about 70 and about 180° C. The naphtha stream 22 may comprise normal paraffins, iso-paraffins, naphthenes, and aromatics. The naphtha stream 22 may be heated to a reaction temperature of between about 300° C. and about 550° C. and preferably between about 325° C. and about 525° C.

The NEP reactor effluent 30 may comprise hydrogen, methane, ethane, propane, and residual C4+. Preferably, the NEP reactor effluent comprises at least 40 wt % ethane or at least 40 wt % propane or at least 70 wt % and preferably at least 80 wt % ethane and propane. The ethane to propane ratio can range from 0.1 to 5. The light paraffin stream can have less than about 15 wt %, suitably less than about 12 wt %, more suitably less than about 10 wt %, preferably less than about 8 wt %, more preferably less than about 6 wt % and most preferably less than about 5 wt % methane. The NEP reactor effluent 30 is passed through coolers, separators for removing the heavier ends and multiple stages of compression and shown collectively as block 31 in FIG. 1. The cooled vapor stream 40 from block 31 passes to a cooling unit, consisting of one or more multi-stream coldbox heat exchangers to produce a feed stream 33 comprising hydrogen, methane, and substantial volumes of ethane and propane, as well as a minor quantity of C4+ hydrocarbons to NEP separation section 34. The deethanizer produces an ethane rich stream (14) and a hydrogen/methane rich stream (72) both of which are routed to ESC 58 to produce an ethylene rich stream 98. The deethanizer 38 DWC also produces a propane rich stream 18 which is sent to depropanizer 66 to produce a purified propane stream 68 and routed to a PDH 106. FIG. 1 is a simplified diagram of the flowscheme. The deethanizer configured as DWC and associated coldbox are the focus of this invention and described in more detail in the following paragraphs.

Figure 2:
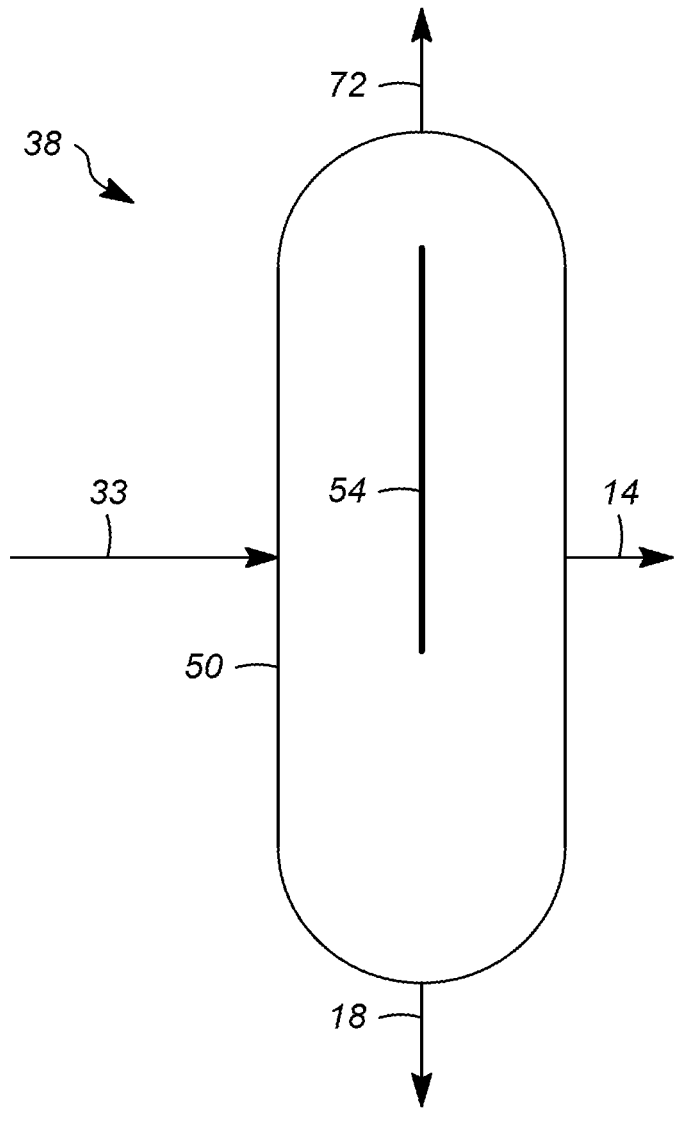
FIG. 2 is a schematic of a separation section of a divided wall fractionation column.
Figure 4:
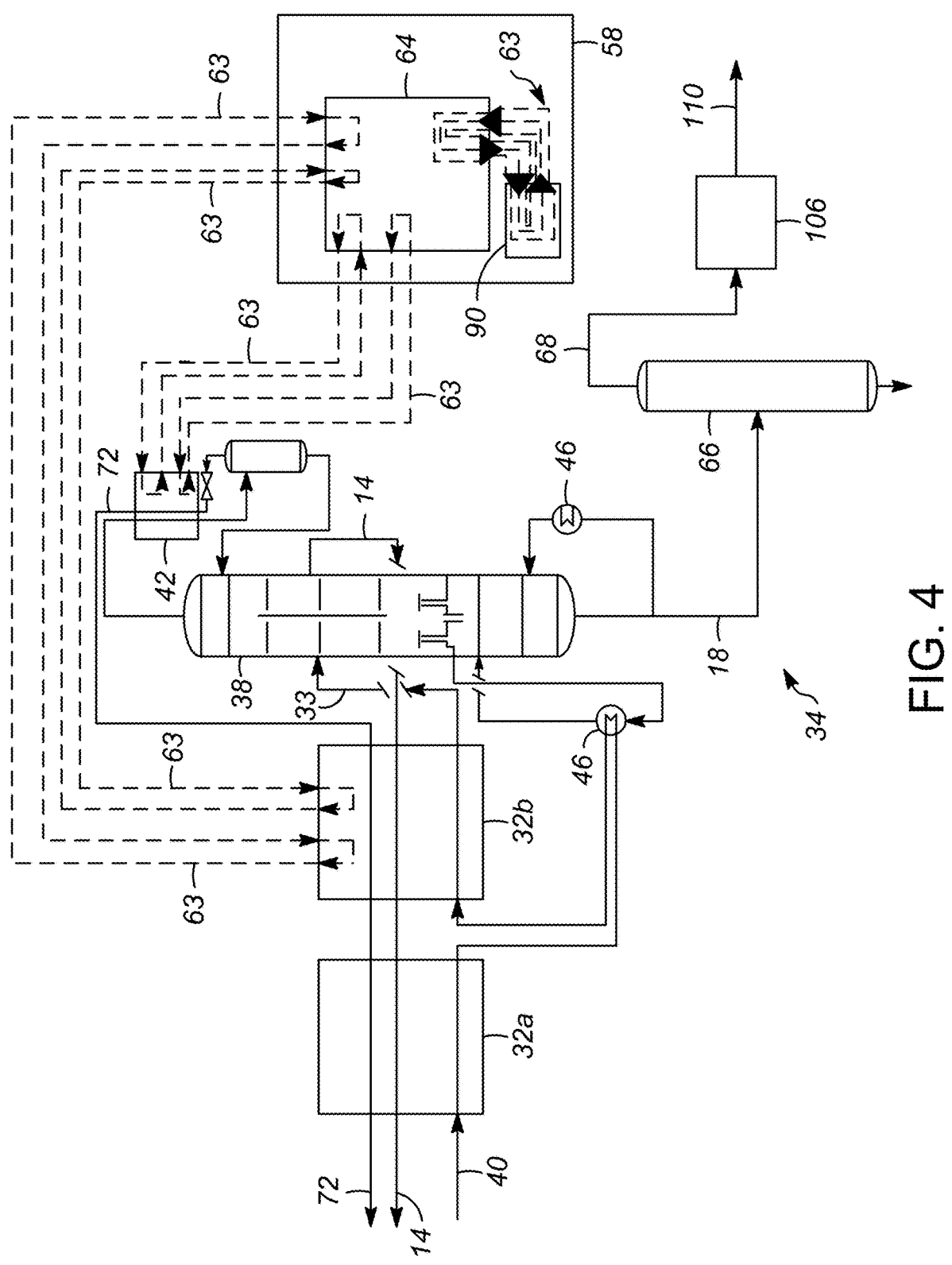
FIG. 4 is a schematic of a naphtha-to-ethane-and-propane processing unit's dividing wall column and the associated coldbox exchangers are shown in detail.

According to the present disclosure, the NEP separation section 34 comprises, among other equipment, a deethanizer 38 and a depropanizer 66 (see FIGS. 1 and 4). The deethanizer 38 is configured as a dividing wall fractionation column and its structure is depicted in FIG. 2. FIGS. 3 and 4 show the deethanizer 38 as a DWC in more detail along with its associated reboilers and condenser. While FIG. 3 shows the location of the DWC in the overall flow scheme and how it is linked to the ESC 58, FIG. 4 shows the DWC and its associated cryogenic exchangers in more detail. The deethanizer 38 DWC is a type of distillation column that can separate mixtures of several components into three or more high-purity streams. The deethanizer 38 DWC requires much less energy, capital investment, and plant space than conventional columns in series or parallel configurations. The concept of the deethanizer 38 DWC is well-established, with much literature focusing on the simulation and control. The deethanizer 38 DWC is a fully thermally coupled distillation column set-up with at least one condenser 42 and at least one reboiler 46 regardless of the number of products. The entire sequence is housed into a single shell 50 by means of one or more vertical partition walls 54 (see FIG. 2 for reference).

Thus, the deethanizer 38 DWC inputs the feed stream 33 and outputs the following streams: (1) a side product of the ethane rich stream 14, which is passed to an ethane producing unit such as the ESC 58, (2) a bottom product 18 comprising a propane rich stream, as well as other heavy products, which is passed to the depropanizer 66, and (3) a top product stream 72 comprising top product stream comprising hydrogen a methane, some slipped (residual) ethane. The coldbox 32 associated with the deethanizer 38 DWC cools the incoming stream to the deethanizer 38 DWC using the cold streams produced from the deethanizer 38 DWC (see FIGS. 3 and 4). The benefits of the feed cooling scheme are shown in Table 1, Example No. 2. The rest of the refrigeration duty of the deethanizer 38 DWC may be provided by one or more refrigeration fluid streams 63 (designated by broken/dashed lines) refrigeration streams flowing from a source of refrigeration fluid streams 64, which is shown in FIG. 3 as residing in the ESC 58; however, it should be understood that this source of refrigeration fluid streams may reside in the NEP processing unit 10 or some other locations as desired.

The ethane rich stream 14 is of relatively high purity and is a vapor side product of the deethanizer 38 DWC. Withdrawing this ethane rich vapor side product from the deethanizer 38 DWC lowers a refrigeration requirement for the deethanizer 38 DWC and reduces energy for vaporization in the ESC 58. In a preferred case, the ethane rich stream 14 is sent to the ESC 58, optionally to the ESC 58 via the coldbox 32*a,b*, and the vapor side product is withdrawn from the DWC eliminates energy for vaporization in the ESC 58. The ethane vapor drawn from the DWC is cold with respect to the feed stream 40 and is therefore utilized to cool the relatively warm (near ambient and approximately) 40° C. feed streams entering the coldbox exchangers in 32*b* and 32*a* (see FIG. 4) from the compression system, followed by coolers and separators. The compression system, coolers and separators are described above.

The ethane rich stream 14 is passed to the ESC 58. Referring to FIG. 3, generally, the ESC 58 includes a cracking heater section 74, a cracked gas compressor section 78, and a chilling section 82. The ethane rich stream 14 is passed from the deethanizer 38 DWC wherein an output stream of the ESC 58 is an ethylene rich stream 87.

The ethane rich stream 14 is initially passed to the cracking heater section 74 of the ESC 58. The ethane rich stream 14 is cracked under steam in the cracking heater section 74 to produce a cracked gas stream (cracking heater effluent) including ethylene, unreacted ethane, hydrogen, methane, and other components. The cracked stream exiting the cracking heater section 74 may be in a superheated state. One or more quench columns 84 are used for quenching or separating the cracked stream into a plurality of cracked streams. Cracking heater effluent from the quench columns 84 is then passed to compression and separation.

Compression of the cracking heater effluent is performed in the cracked gas compression section 78. Carbon dioxide and acidic sulfur compounds are removed from the cracked gas in a caustic scrubber 86. The compressed cracking heater effluent is cooled and subsequently dried in a dryer 88 by molecular sieves that remove most of the water.

The dried cracking heater effluent 89 is passed to a cooling unit such as a coldbox 90. Hydrogen and light hydrocarbons are removed from the cracked gas in the coldbox 90. Condensates from the coldbox 90 are fed to a series of separation columns 91, 92.

In a first column 91, a methane stream 93 is obtained from the top and passed to the coldbox 90, while a bottom stream is fed to a second column 92, which is a deethanizer.

A top product of the second column 92, composed primarily of ethylene and ethane, is fed to an acetylene converter 94 and then fractionated in a C2-splitter 96.

An ethylene stream 87 is withdrawn from the C2-splitter 96 as a side product. Ethane, from C2-splitter bottom product 99, is recycled to the cracking heater section 74

The top product stream 72 of the deethanizer 38 DWC comprises a stream comprising hydrogen, methane, and some slipped (residual) ethane. Thus, some ethane components are allowed to slip with the top product stream 72. The amount of ethane components allowed to slip is adjusted and controlled to optimize overhead temperature and refrigeration requirements. For example, recovering 90% of ethane feed to DWC in side product of DWC vs. 97%—recovery results in approximately −47° C. (52° F.) overhead temperature of DWC against −71° C. (−96° F.) for the latter case. The result is deeper refrigeration for the latter case, requiring 20-25% higher refrigeration compressor power for the NEP attributable to NEP requirements. The top product stream 72 bypasses the cracking heater section 74 and is passed to the cracked gas compressor 78 of the ESC 58. In this way, the chilling section 82 of the ESC 58 is utilized to recover and separate the hydrogen and methane. This allows additional chilling section equipment for recovery of hydrogen and methane to be eliminated from the NEP separation section 34. The slipped ethane in the top produce stream helps to keep the DWC overhead temperature higher than would be possible with minimum ethane slippage and this in turn helps to reduce refrigeration compressor power attributable to NEP requirements.

As shown in FIG. 4, the top product stream 72 may be passed to the NEP coldbox 32*b* prior to passing to the ESC 58.

The ethane in the top product stream 72 that bypasses the cracking heater section 74 is recovered in an ESC C2-splitter 96 downstream from the cracked gas compressor 78, the ESC coldbox 90, and ESC columns 91 (demethanizer), 92 (deethanizer). Optimizing the ethane slippage with the DWC top product stream 72 in conjunction with energy required for separation of additional ethane in the ESC C2-splitter 96. It is contemplated that the ethane slippage can be varied between 1% to 20% of the net ethane produced in the NEP processing unit 10.

The net bottom product 18 withdrawn from the deethanizer 38 DWC comprises a stream comprising propane and C4s as well as other heavy products. As shown in FIG. 4, the bottom product 18 is passed to a depropanizer column 66. A propane rich stream 68 is fed to propane dehydrogenation unit (PDH) 106. A propane rich stream 68 is withdrawn as net top product from the depropanizer 66 and sent to the PDH 106, where the desired propylene product 110 is output.

According to the present disclosure, the ethane rich stream 14 passed to the ESC 58 and the propane stream 18 passed to the PDH 106 produce higher quantities of olefins (ethylene and propylene) due to the DWC (helps to produce ethane and propane rich streams by effective separation), than what would be possible if naphtha was directly fed to a naphtha cracker to produce olefins. The other novelties and advantages of the proposed scheme are elaborated in the subsequent sections.

However, the products of the NEP reactor 26 contain light products, e.g., hydrogen and methane, along with ethane and propane. As shown in FIG. 1, and as discussed in the preceding sections, the NEP processing unit 10 with incorporation of a DWC type deethanizer 38 and using shared refrigeration equipment with an ESC (see FIGS. 3-5) is a cost-efficient method of separating H2 and CH4 from ethane and propane produced in NEP reactor 26. Careful separation of streams produced in the NEP reactor section 26 together with using the coldbox 90 of the ESC 58 to separate H2 from CH4 which was produced in the NEP processing unit 10, makes this scheme of using shared assets between NEP processing unit 10 and the ESC 58 optimal regarding both operating and capital expenses.

Advantages of employing the deethanizer 38 DWC in this process include a reduction in overall energy usage. The DWC system is 15% more efficient than traditional two-column systems. Also, the DWC system reduces the equipment count compared to an alternative flow scheme using membrane systems. Utilizing the deethanizer 38 DWC is an innovative way to achieve the separation of: (1) hydrogen/H4 rich gas as a top product stream 72; (2) an ethane rich 14 stream as a side product; and (3) a propane rich stream 18 as the bottom product 18.

It is further contemplated that the principles of this disclosure result in greater carbon efficiency (>70%) that prior processes (45%-55%). Corresponding lower by-product yields and 40%-70% lower fuel gas make the process disclosed herein hydrogen self-sufficient. Finally, the process of this disclosure improves flexibility at design stage for high P:E (propylene to ethylene ratio) to low P:E with catalyst and processing condition change in the NEP reactor section.

Further according to this disclosure, C2 components are allowed to slip with the top product stream 72. The amount or volume of C2 allowed to slip is controlled. This allows optimization of the overhead temperature and refrigeration requirements and thus helps to reduce the overall energy usage.

The hydrogen and methane rich stream is passed to the cracked gas compressor section 78 and further on to the ESC cooling/separation section, bypassing the cracking heater section 74 since these components are not desired feed for the cracking heaters of the ESC 58. In this way the ESC cooling unit (coldbox 90, is utilized to recover the H2 and the CH4). Thus, the need for additional cooling units for recovery and separation of H2 and CH4 is eliminated in the NEP separation section 34.

The C2s in the hydrogen rich stream which bypass the ESC cracking heater section 74 are recovered in the ESC C2-splitter 96. Optimizing the C2 slippage with deethanizer 38 DWC top product stream 72 stream optimizes energy required for separation in the ESC 58 C2-splitter 96. The C2 slippage can be varied between 5% to 20% of the net C2s produced in the NEP processing unit 10.

The disclosed process is approximately 15% more energy efficient when compared to a traditional two column process system.

The DWC helps to eliminate hydrogen and CH4 entering the ESC cracking heater section 74 with feed ethane. This is not possible in other alternative systems. Approximately 10%-15% volumetric flow reduction through the ESC heaters result with consequent benefits in capex of heaters and associated equipment. This also results in separation of components which do not result in ethylene production in cracking heaters in ESC.

According to the present disclosure, cold streams and the deethanizer 38 DWC reboiler 46 may be used for heat recovery. There is additional heat recovery from the cold ethane rich stream 14 and hydrogen stream 72 coming out of the deethanizer 38 DWC. The balance of the cooling may be derived from the refrigeration system which may be common for the ESC 58 and NEP 10 and shown as 64. Cooling may be shared between the ESC 58 and the NEP processing unit 10. A refrigeration system including compressors can be located in the ESC 58 and are shown as 64, and the NEP coldbox 32 can derive the refrigerant fluid flow as required. NEP coldbox 32 refrigeration requirement is approximately 25% of the ESC coldbox 90 requirement.

The system is flexible towards the refrigeration system selected for the ESC 58 and both mixed refrigeration system (MR) or cascade (ethylene-propylene) refrigeration system can be used.

This disclosure is further directed to integration of the NEP processing unit 10 comprising the deethanizer 38 DWC with the ESC 58. The integration disclosed herein achieves a passing of the ethane rich stream 14 produced in the NEP processing unit 10 to the cracking heater section 74 of the ESC 58. The integration further achieves passing the top product stream 72 of hydrogen, methane, and residual ethane slipped from the deethanizer 38 DWC top to the cracked gas compressor section 78 of the ESC 58. The hydrogen and the methane are separated in the coldbox 90 and demethanizer 91 respectively of the ESC 58 while the ethane rich stream is eventually separated in the C2-splitter bottom product 99 and passed to the ethane cracking heater section 74 of the ESC 58. The ethane content in this stream is about 1% to 20% of the total ethane produced in the NEP reactor 26, which is passed to the deethanizer 38 DWC as feed. The NEP processing unit 10 and the ESC 58 can use shared refrigeration equipment.

According to the present disclosure, the NEP processing unit 10 and the ESC 58 can share a common refrigeration system with a common source of refrigeration fluid(s) 64. One or more refrigeration fluids 63 are passed from the common source of refrigeration fluid(s) 64 to a coldbox 32 of the NEP processing unit 10 and to a coldbox 90 of the ESC 58. FIG. 4 shows 2 levels of cascade propylene-ethylene refrigeration (propylene refrigerant may be of approximately −4° C. and drawn $3^{rd}$ stage suction and of approximately −16° C. and drawn from $2^{nd}$ stage suction) for NEP coldbox 32b while the DWC condenser 42 shows 1 level of ethylene refrigeration (may be of approximately −45° C. drawn from 3rd stage suction) and 1 level of propylene (may be approximately −37° C. and drawn from first stage). The ESC coldbox 90 has multiple levels of cascade ethylene-propylene refrigeration but not shown, for simplicity and since this coldbox 90 is not the focus of the present disclosure. The focus and the illustrations are intended to show that NEP refrigeration requirements can make use of available and appropriate refrigeration streams available for the ESC coldbox 90, which is the main user of the refrigeration streams, as explained above. Hence, it is emphasized that the cascade refrigeration system of ethylene-propylene and the temperature levels indicated above can vary by approximately +5° C. and also as required to get the desired separation in DWC, and the design of the NEP coldbox 32*a,b* and the DWC condenser 42 can be configured to make use of the available levels of refrigeration. The cascade ethylene-propylene refrigeration system could also be replaced by single mixed refrigeration system for both NEP and ESC.

Figure 5:
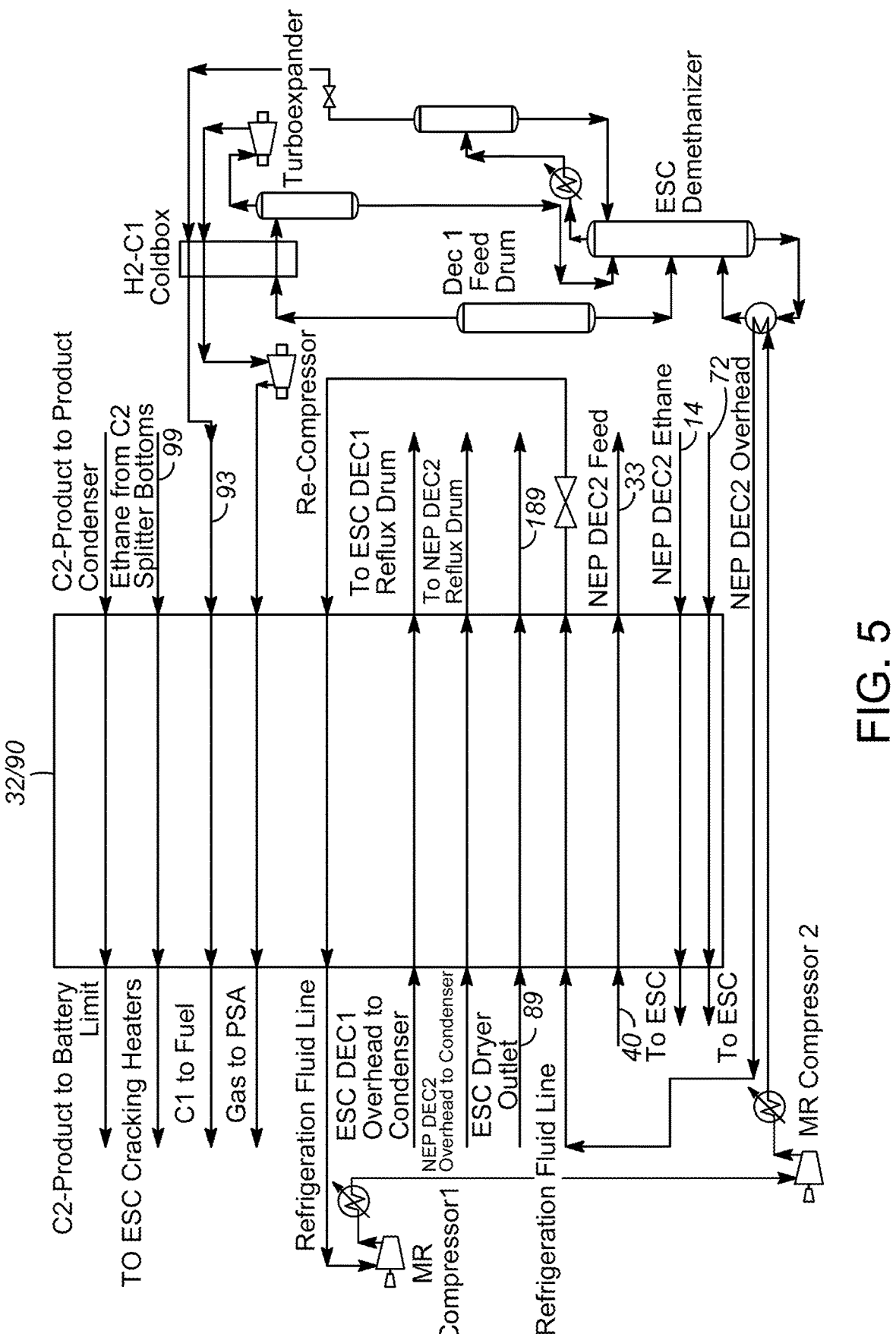
FIG. 5 is a schematic of a common coldbox and a mixed refrigeration system (MR) provided to integrate a naphtha-to-ethane-and-propane processing unit with an ethane steam cracker.

Alternatively, referring to FIG. 5, it is contemplated that the NEP processing unit 10 and the ESC 58 can share a common coldbox 32/90 and a common mixed refrigeration system (MR). This cold box will process all the cold streams of the NEP processing unit 10 and the ESC 58 and use these streams to cool the incoming warm streams that need to be cooled. Here, on the NEP processing unit 10 side of the common coldbox 32/90, the NEP reactor section effluent stream 40 passes through the common coldbox 32/90 to become the cooled feed stream 33 to the deethanizer 38 DWC; the top net vapor product stream 72 passes through the common coldbox 32/90 and is warmed prior to passing to the ESC 58; the ethane rich stream 14 passed from the deethanizer 38 DWC passes through the common coldbox 32/90 and is warmed prior to passing to the ESC 58; the NEP DWC overhead stream (not numbered) is cooled and condensed before entering the NEP DWC reflux drum (not numbered). The ESC 58 side of the common coldbox 32/90 receives the dried cracking heater effluent stream 89 from the dryer 88 and is cooled to stream 189 to be fed to ESC demethanizer 91; the methane stream 93 from top of the first column (demethanizer) 91 enters the common coldbox 32/90 and is warmed and sent to fuel gas. There are many other streams originating in the ESC 58, such as cold hydrogen rich gas originating in the ESC 58 and sent as warmed hydrogen rich gas, possibly to PSA; an ESC demethanizer overhead stream is condensed and is sent to a demethanizer condenser; an ethane rich stream from the ESC C2 splitter 96 bottoms and is warmed and sent to ESC Cracking heaters 74; liquid ethylene product is vaporized in coldbox 32/90 and sent to a desired destination. The unbalanced refrigeration requirement can be met by mixed refrigeration system. The intent is to design an integrated common coldbox 32/90 for both NEP processing unit 10 and the ESC 58 and have a common mixed refrigeration system also.

While the specific embodiments have been illustrated and described, numerous modifications come to mind without significantly departing from the spirit of the invention, and the scope of protection is only limited by the scope of the accompanying Claims.

TABLE 1

OPEX BENEFITS OF DWC SCHEME IN NEP FRACTIONATION SECTION

| Example No. | Item Description | Benefits | Remarks on Benefits |
|---|---|---|---|
| 1 | Energy benefit - DWC relative to conventional two column system | 0.85 base | Base = Energy usage with a two column system |
| 2 | Energy benefit - with heat integration in NEP cold box relative to no heat integration | 30% reduction for DWC feed cooling duty 5% reduction for DWC condenser duty | |
| 3 | Energy benefits: (Overhead condenser duty reduction) for vapor side draw relative to liquid side draw in DWC | 0.4 to 0.45 of Base | Base = Condenser duty with a liquid side draw. All other column operation parameters (Vapor side draw vs liquid side draw) being comparable |
| 4 | Reduction in volumetric flow to Ethane Cracking Heaters due to separation of H2 and methane in DWC overhead | 15% reduction | Approximately 15% reduction in volumetric flow to ethane cracking heaters due to separation of H2/methane in DWC overhead H2/Methane do not crack to result in ethylene make in ethane crackers |
| 5 | Energy benefit: higher DWC overhead temperature with Ethane slip relative to without Ethane slip and consequent reduced refrigeration duty | 0.75 of base to 0.85 of base @ 90% C2 recovery in DWC side product compared to 97% C2 recovery (considered as base) | C2 slip in overhead allows higher DWC overhead temperature -- which in turn means lower power usage of refrigeration compressors. 90% C2 recovery results in −47° C./−52° F. overhead temperature where as 97% C2 recovery (implying purer H2/CH4 in DWC overhead) results in −71° C./−96° F. DWC overhead temperature -- all other parameters being comparable. The higher DWC overhead temperature results in reduced refrigeration compression power (75% to 80% of BASE; |

TABLE 1-continued

OPEX BENEFITS OF DWC SCHEME IN NEP FRACTIONATION SECTION

| Example No. | Item Description | Benefits | Remarks on Benefits |
|---|---|---|---|
| | | | where BASE = NEP refrigeration compressor power at 97% C2 recovery as DWC side product C2 slippage in DWC overhead can be looked in conjunction with additional separation needs in ESC C2 Splitter |

TABLE 2

CAPEX BENEFITS DUE TO INTEGRATION
BETWEEN NEP AND ESC

| Example No. | Configuration | Benefits |
|---|---|---|
| 1 | Separate cold boxes for NEP and ESC but using common refrigeration system | Eliminates need for separate refrigeration system (refrigeration compressor with drivers, suction drum, some exchangers Reduce CAPEX of NEP Reduce plot area Easy to design and execute Refrigeration needs will be primarily governed by ESC, and NEP will be supplied with refrigeration streams |
| 2 | Use ESC cold box to separate H2 and Methane generated in NEP | Avoids need for deep refrigeration and system to separate hydrogen from methane in NEP fractionation section Eliminates need for independent H2/methane separation system within NEP (reduced cold box exchangers, deep refrigeration equipment) Reduced CAPEX for NEP by synergizing separation requirement of NEP and ESC |

SPECIFIC EMBODIMENTS

While the following is described in conjunction with specific embodiments, it will be understood that this description is intended to illustrate and not limit the scope of the preceding description and the appended claims.

A first embodiment of the invention is a process of producing ethylene and propylene from naphtha, the process comprising producing light paraffins—ethane, hydrogen/methane/residual ethane and propane rich streams—in a dividing wall fractionation column from a stream of hydrogen, methane, propane, and residual C4+ produced in the reactor section of a naphtha-to-ethane-and-propane processing unit by reacting naphtha with hydrogen comprising cooling a naphtha reactor effluent stream produced by a naphtha reactor of the naphtha-to-ethane-and-propane processing unit to produce a feed stream; passing the feed stream to a dividing wall fractionation column; passing an ethane stream from the dividing wall fractionation column to an ethane steam cracker to produce a cracking heater effluent stream; passing the cracking heater effluent stream to a coldbox of the ethane steam cracker after multiple steps such as quenching, compression, cooling, caustic scrubbing, drying; wherein one or more fluids for cooling the naphtha (NEP) reactor effluent stream and for cooling the coldbox of the ethane steam cracker are provided by a common refrigeration system. The process of claim 1 further comprising providing a separate coldbox in the naphtha-to-ethane-and-propane processing unit through which the naphtha reactor effluent stream passes during the cooling step. The process of claim 2 wherein the one or more fluids for cooling the naphtha reactor effluent stream comprises two multiple levels of cascade refrigeration or mixed refrigeration The process of claim 3 further comprising passing a top product stream comprising hydrogen, methane, and residual ethane from the dividing wall fractionation column to the ethane steam cracker; and passing the top product stream through a condenser and the separate coldbox for exchanging heat prior to routing to the ethane steam cracker. The process of claim 4 wherein the top product stream bypasses a cracking heater section of the ethane steam cracker and is passed to a cracked gas compressor section of the ethane steam cracker. The process of claim 5 further comprising passing the top product stream through the separate coldbox prior to passing the top product stream to the ethane steam cracker. The process of claim 6 wherein the feed stream comprises hydrogen, methane, ethane, and propane and residual C4+. The process of claim 7 further comprising passing the cracking heater effluent stream through a series of steps comprising quenching, compressing, cooling, caustic scrubbing, and drying prior to passing the cracking heater effluent stream to the coldbox of the ethane steam cracker. The process of claim 8 wherein a hydrogen stream is separated due to the cooling in the cold box and a methane stream is separated in demethanizer and both streams are passed via the coldbox. The process of claim 1 further comprising passing the naphtha reactor effluent through the coldbox to cool the naphtha reactor effluent. The process of claim 10 further comprising passing a top product stream comprising hydrogen, methane, and residual ethane from the dividing wall fractionation column to the ethane steam cracker. The method of claim 11 further comprising passing the top product stream through the coldbox prior to passing the top product stream to the ethane steam cracker. The process of claim 12 further comprising passing the top product stream through a condenser prior to passing the top product stream to coldbox and wherein the top product stream is passed to a cracked gas compressor section of the ethane steam cracker. The process of claim 13 wherein the feed stream comprises hydrogen, methane, ethane, and propane and residual C4+.

A second embodiment of the invention is a process of producing ethylene and propylene from naphtha, the process comprising producing light paraffins from naphtha in NEP reactor resulting in a reactor effluent stream comprising hydrogen, methane, ethane, propane and C4+ components, the process comprising cooling a naphtha reactor effluent stream produced by a naphtha reactor of a naphtha processing unit to produce a feed stream; passing the feed stream to a dividing wall fractionation column; passing a top product stream comprising hydrogen, methane, and residual ethane from the dividing wall fractionation column to an ethane steam cracker. The process of claim 15 wherein the top product stream bypasses a cracking heater section of the ethane steam cracker and is passed to a cracked gas compressor section of the ethane steam cracker. The process of claim 16 further comprising passing the top product stream through a coldbox prior to passing the top product stream to the ethane steam cracker and passing the top product stream through a condenser prior to passing the top product stream to the coldbox. The process of claim 17 wherein the feed stream comprises hydrogen, methane, ethane, and propane and residual C4+. The process of claim 18 further comprising passing an ethane stream from the dividing wall fractionation column to an ethane steam cracker to produce a cracking heater effluent stream; passing the cracking heater effluent stream through a series of steps comprising quenching, compressing, cooling, caustic scrubbing, and drying prior to passing the cracking heater effluent stream to the coldbox of the ethane steam cracker. The process of claim 19 wherein a hydrogen stream is separated due to the cooling in the cold box and a methane stream is separated in demethanizer and both streams are passed via the coldbox.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process of producing ethylene and propylene from naphtha, the process comprising:
  reacting naphtha with hydrogen in a reactor section of a naphtha-to-ethane-and-propane (NEP) processing unit to produce a naphtha reactor effluent stream comprising hydrogen cooling methane, ethane, propane and C4+ hydrocarbons;
  cooling the naphtha reactor effluent stream to produce a feed stream;
  passing the feed stream to a dividing wall fractionation column to produce a top product stream comprising hydrogen, methane, and residual ethane, an ethane stream, and a propane stream;
  passing the ethane stream from the dividing wall fractionation column to a cracking heater section of an ethane steam cracker to produce a cracking heater effluent stream comprising ethylene;

passing the propane stream to a propane de-hydrogenation unit to produce an effluent stream comprising propylene; and
  passing the cracking heater effluent stream to a coldbox of the ethane steam cracker;
  wherein one or more fluids for cooling the naphtha reactor effluent stream and for cooling the coldbox of the ethane steam cracker are provided by a common refrigeration system.

2. The process of claim 1 further comprising providing a separate coldbox in the naphtha-to-ethane-and-propane processing unit through which the naphtha reactor effluent stream passes during the cooling step.

3. The process of claim 2 wherein the one or more fluids for cooling the naphtha reactor effluent stream comprises two multiple levels of cascade refrigeration or mixed refrigeration.

4. The process of claim 3 further comprising passing the top product stream from the dividing wall fractionation column to the ethane steam cracker; and passing the top product stream through a condenser and the separate coldbox for exchanging heat prior to routing to the ethane steam cracker.

5. The process of claim 4 wherein the top product stream bypasses the cracking heater section of the ethane steam cracker and is passed to a cracked gas compressor section of the ethane steam cracker.

6. The process of claim 5 wherein the feed stream comprises hydrogen, methane, ethane, propane, and residual C4+ hydrocarbons.

7. The process of claim 6 further comprising passing the cracking heater effluent stream through a series of steps comprising quenching, compressing, cooling, caustic scrubbing, and drying prior to passing the cracking heater effluent stream to the coldbox of the ethane steam cracker.

8. The process of claim 7 wherein a hydrogen stream is separated due to the cooling in the coldbox and a methane stream is separated in a demethanizer and both streams are passed via the coldbox.

9. The process of claim 1 further comprising passing the naphtha reactor effluent through the coldbox to cool the naphtha reactor effluent.

10. The process of claim 9 further comprising passing the top product stream from the dividing wall fractionation column to the ethane steam cracker.

11. The method of claim 10 further comprising passing the top product stream through the coldbox prior to passing the top product stream to the ethane steam cracker.

12. The process of claim 11 further comprising passing the top product stream through a condenser prior to passing the top product stream to the coldbox and wherein the top product stream is passed to a cracked gas compressor section of the ethane steam cracker.

13. The process of claim 12 wherein the feed stream comprises hydrogen, methane, ethane, propane, and residual C4+ hydrocarbons.

14. A process of producing ethylene and propylene from naphtha, the process comprising:
  reacting naphtha with hydrogen in a reactor of a naphtha-to-ethane-and-propane (NEP) processing unit to produce a naphtha reactor effluent stream comprising hydrogen, methane, ethane, propane and C4+ hydrocarbons;
  cooling the naphtha reactor effluent stream to produce a feed stream;
  passing the feed stream to a dividing wall fractionation column to produce a top product stream comprising hydrogen, methane, and residual ethane, an ethane stream, and a propane stream;

passing the top product stream from the dividing wall fractionation column to an ethane steam cracker to produce a cracking heater effluent stream comprising ethylene; and passing the propane stream to a propane de-hydrogenation unit to produce an effluent stream comprising propylene.

15. The process of claim 14 wherein the top product stream bypasses a cracking heater section of the ethane steam cracker and is passed to a cracked gas compressor section of the ethane steam cracker.

16. The process of claim 15 further comprising passing the top product stream through a coldbox prior to passing the top product stream to the ethane steam cracker and passing the top product stream through a condenser prior to passing the top product stream to the coldbox.

17. The process of claim 16 wherein the feed stream comprises hydrogen, methane, ethane, and propane and residual C4+ hydrocarbons.

18. The process of claim 17 further comprising passing the ethane stream from the dividing wall fractionation column to a cracking heater section of the ethane steam cracker to produce a cracking heater effluent stream; passing the cracking heater effluent stream through a series of steps comprising quenching, compressing, cooling, caustic scrubbing, and drying prior to passing the cracking heater effluent stream to a coldbox of the ethane steam cracker.

19. The process of claim 18 wherein a hydrogen stream is separated due to the cooling in the coldbox of the ethane steam cracker and a methane stream is separated in a demethanizer and both streams are passed via the coldbox of the ethane steam cracker.

* * * * *